Figure 1:
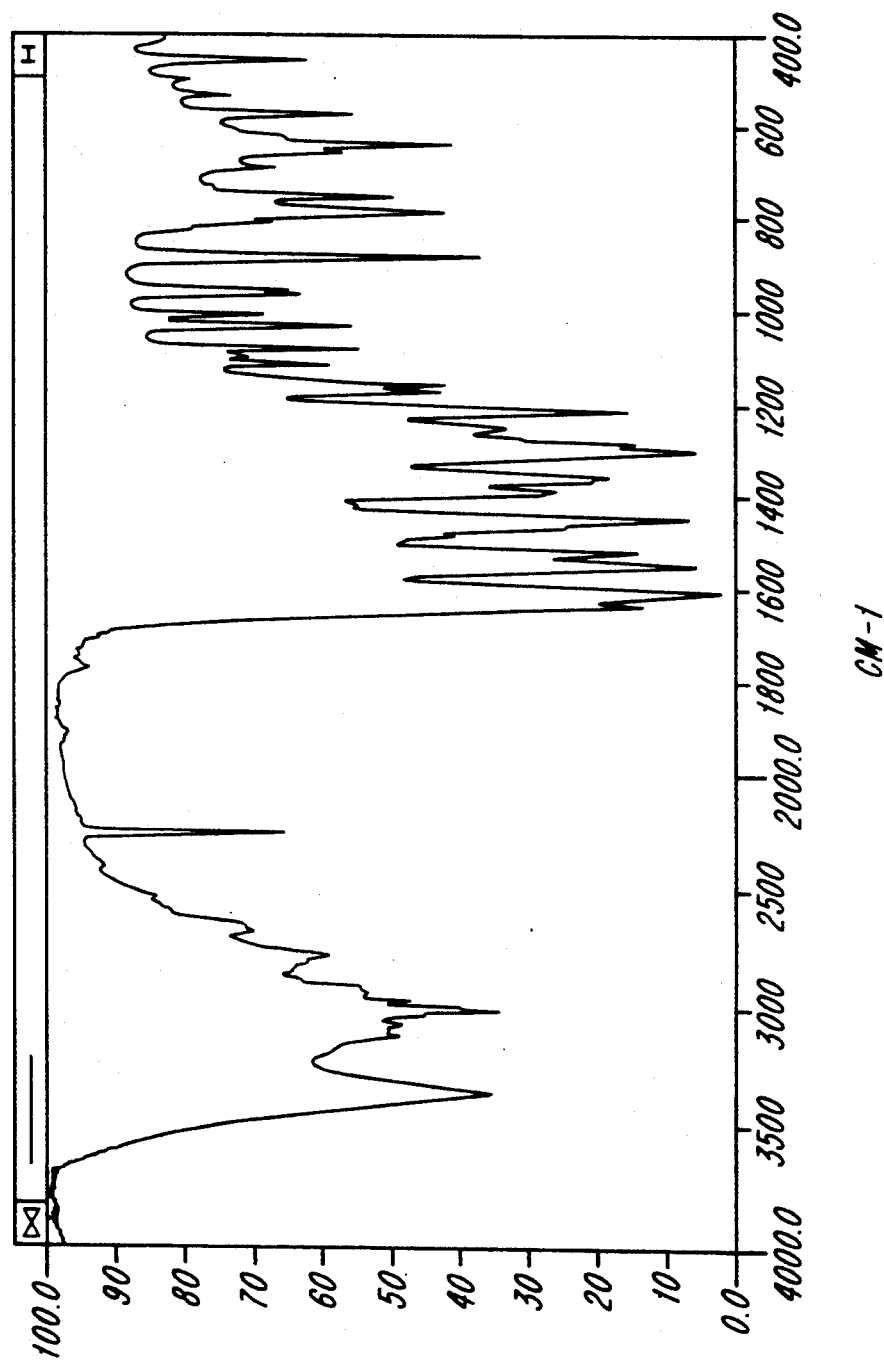

United States Patent [19]
Pippuri et al.

[11] Patent Number: 5,135,950
[45] Date of Patent: Aug. 4, 1992

[54] STABLE POLYMORPHIC FORM OF (E)-N,N-DIETHYL-2-CYANO-3-(3,4-DIHYDROXY-5-NITROPHENYL)ACRYLAMIDE AND THE PROCESS FOR ITS PREPARATION

[75] Inventors: Aino K. Pippuri, Espoo; Erkki J. Honkanen, Vantaa; Jorma V. Haarala, Helsinki, all of Finland

[73] Assignee: Orion-yhtymä Oy, Espoo, Finland

[21] Appl. No.: 606,717

[22] Filed: Oct. 31, 1990

[30] Foreign Application Priority Data

Nov. 3, 1989 [GB] United Kingdom ............ 8924838.9

[51] Int. Cl.⁵ ................... A61K 31/275; C07C 255/07
[52] U.S. Cl. ..................................... 514/521; 558/401
[58] Field of Search .................... 558/401; 514/521

[56] References Cited

U.S. PATENT DOCUMENTS

| | | | |
|---|---|---|---|
| 4,963,590 | 10/1990 | Bäckström et al. | 514/678 |
| 4,971,996 | 11/1990 | Shiraishi et al. | 558/401 |

FOREIGN PATENT DOCUMENTS

| | | |
|---|---|---|
| 0339671 | 11/1989 | European Pat. Off. . |
| 2039558 | 2/1987 | Japan . |
| 2200109A | 7/1988 | United Kingdom . |

*Primary Examiner*—Joseph Paul Brust
*Attorney, Agent, or Firm*—Burns, Doane, Swecker & Mathis

[57] ABSTRACT

Stable and crystallographically essentially pure polymorphic form A of (E)-N,N-diethyl-2-cyano-3-(3,4-dihydroxy-5-nitro-phenyl)acrylamide may be prepared by crystallizing crude synthesis product from lower aliphatic carboxylic acid such as formic or acetic acid with a catalytic amount of hydrochloric or hydrobromic acid added. The product is a potent inhibitor of catechol-O-methyl-transferase enzyme (COMT).

10 Claims, 2 Drawing Sheets

STABLE POLYMORPHIC FORM OF (E)-N,N-DIETHYL-2-CYANO-3-(3,4-DIHYDROXY-5-NITROPHENYL)ACRYLAMIDE AND THE PROCESS FOR ITS PREPARATION

The present invention relates to the stable and crystallographically essentially pure polymorphic form of N,N-diethyl-2-cyano-3-(3,4-dihydroxy-5-nitrophenyl) acrylamide E-isomer, denoted (E)-N,N-diethyl -2-cyano-3-(3,4-dihydroxy-5-nitrophenyl) acrylamide A, and to a process for the preparation thereof.

N,N-Diethyl-2-cyano-3-(3,4-dihydroxy-5-nitrophenyl) acrylamide described in British patent application No. 8727854 by the applicant is a potent inhibitor of catechol-O-methyl-transferase enzyme (COMT) and may be used pharmaceutically in the treatment of e.g., Parkinson's disease. This compound with a melting point of 153-156° C. has proven to be a mixture of two geometric isomers, E- and Z-isomers (70-80% E-isomer and 30-20% Z-isomer) having formulae:

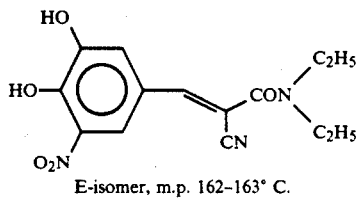

E-isomer, m.p. 162-163° C.

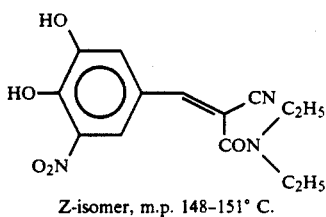

Z-isomer, m.p. 148-151° C.

(E)-N,N-Diethyl-2-cyano-3-(3,4-dihydroxy-5-nitrophenyl) acrylamide (I) may exist at least in two polymorphic forms A and B as shown by X-ray crystallography. The Z-isomer as well as the polymorphic form B of the E-isomer have been shown to be unstable. The Z-isomer is transformed readily into the E-isomer under the influence of heat or acids. Similarly the polymorphic form B of the E-isomer isomerizes slowly to the polymorphic form A on standing at room temperature. On recrystallization of the crude synthesis product from conventional solvents such as lower aliphatic alcohols, esters or hydrocarbons, e.g., ethanol, 2-propanol, ethyl acetate or toluene, a very complicated mixture of different geometric isomers and/or polymorphic forms are generally obtained which interfere with the characterization and standardization of the drug substance. The polymorphism and geometrical isomerism may also influence the bioavailability of the drug.

Surprisingly, it has now been observed that crystallographically essentially pure and stable polymorphic form A of (E)-N,N-diethyl-2-cyano-3-(3,4-dihydroxy-5-nitrophenyl)acrylamide is obtained in good yield, when the crude product of synthesis is recrystallized from lower aliphatic carboxylic acid such as formic or acetic acid with a catalytic amount of hydrochloric or hydrobromic acid added. This method allows large scale production of homogenous and crystallographically essentially pure polymorphic form A of (E)-N,N-diethyl-2-cyano-3-(3,4-dihydroxy-5-nitrophenyl)acrylamide independent of batch size or cooling rate.

"Crystallographically essentially pure" when used herein means the polymorphic form A of (E)-N,N-diethyl-2-cyano-3-(3,4-dihydroxy-5-nitrophenyl) acrylamide containing a maximum of 3% and preferably a maximum of 2% of other polymorphic forms or the Z-isomer.

"Lower aliphatic-carboxylic acid" means here aliphatic carboxylic acid having 1-2 carbon atoms. Examples are formic and acetic acid.

The polymorphic form A of (E)-N,N-diethyl-2-cyano-3-(3,4-dihydroxy-5-nitrophenyl)acrylamide is characterized either by IR-spectrometry or X-ray crystallography. IR-spectrum of the polymorphic form A of (E)-N,N-diethyl-2-cyano-3-(3,4-dihydroxy-5-nitrophenyl) acrylamide is seen in FIG. 1 and the typical IR-absorption bands are presented in Table 1.

TABLE 1

Typical IR-absorption bands of the polymorphic form A of (E)-N,N-diethyl-2-cyano-3-(3,4-dihydroxy-5-nitrophenyl) acrylamide

| Wave numbers ($cm^{-1}$) and the relative intensities of absorption bands | Assignment of the vibrational modes |
| --- | --- |
| 3339 s | O—H stretching |
| 3092 w | C—H stretching, |
| 3066 w | aromatic and |
| 3039 w | unsaturated |
| 2981 w | C—H stretching, |
| 2938 w | saturated |
| 2217 m | CN stretching |
| 1628 s | tertiary amide C=O stretching |
| 1607 s | C=C stretching, |
| 1580 sh | conjugated with C=O and aromatic ring; and C=C stretching, aromatic |
| 1544 s | $NO_2$ asymmetric stretching |
| 1512 m | C=C stretching, aromatic |
| 1441 s | $CH_2$ bending; asymmetric $CH_3$ bending; C=C stretching, aromatic |
| 1377 s | $NO_2$ symmetric stretching; OH bending |
| 1298 s | C—O stretching |
| 1281 sh | |
| 1210 m | C—H bending, |
| 1165 m | aromatic |
| 1150 m | |
| 800 sh | C—H out of plane bending, aromatic |
| 779 m | |
| 740 m | |
| Experimental | |
| Instrument: | Perkin-Elmer FTIR 1725X |
| Detector: | TGS |
| ordinate mode: | % T |
| Abscissa mode: | Wave numbers ($cm^{-1}$) |
| Resolution: | 4 $cm^{-1}$ |
| Number of scans: | 20 |
| Phase: | KBr | s = strong; m = medium; w = weak; sh = shoulder

Figure 2:
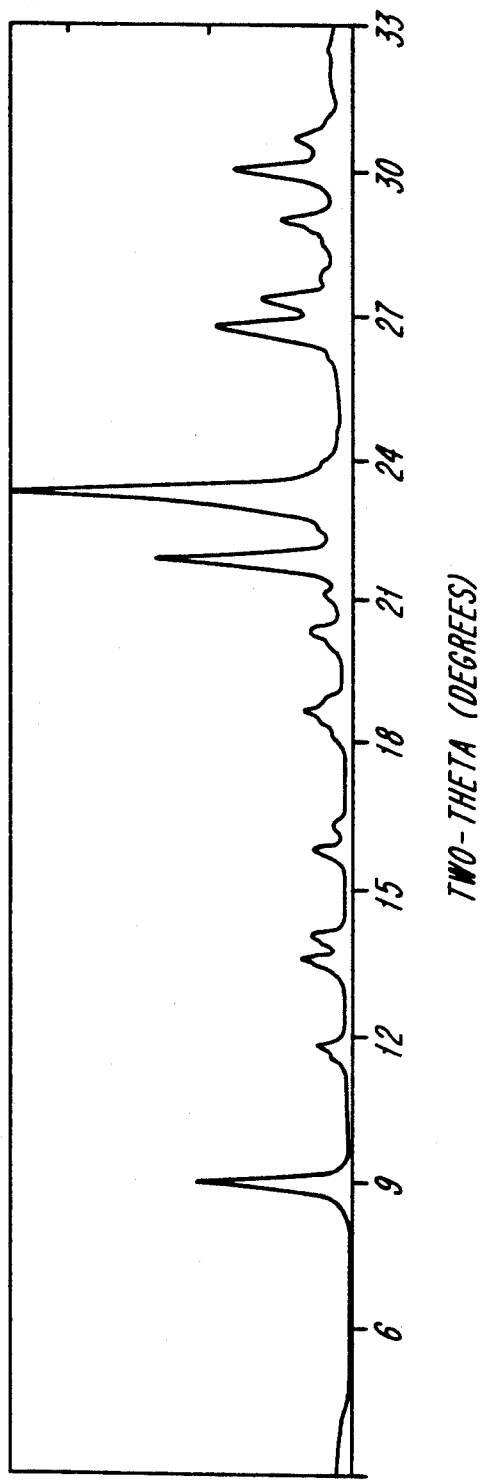

The X-ray powder diffraction patterns of the polymorphic form A of (E)-N,N-diethyl-2-cyano-3-(3,4-dihydroxy -5-nitrophenyl)acrylamide are seen in FIG. 2 and the crystallographic data in Table 2.

TABLE 2

Crystallographic data of polymorphic form A

TABLE 2-continued of (E)-N,N-diethyl-2-cyano-3-(3,4-di-
hydroxy-5-nitrophenyl)acrylamide
Peak positions (2θ), interplanar spacings (d) and
relative peak intensities of the first 20 reflections.

| No | 2θ | d | Rel I (%) |
|---|---|---|---|
| 1 | 3.680 | 23.9905 | 0.8 |
| 2 | 9.040 | 9.7745 | 49.7 |
| 3 | 11.840 | 7.4685 | 9.9 |
| 4 | 13.541 | 6.5339 | 11.1 |
| 5 | 14.060 | 6.2939 | 11.6 |
| 6 | 15.820 | 5.5974 | 7.6 |
| 7 | 16.320 | 5.4270 | 3.9 |
| 8 | 18.220 | 4.8651 | 4.6 |
| 9 | 18.459 | 4.8027 | 8.7 |
| 10 | 18.720 | 4.7363 | 13.6 |
| 11 | 18.940 | 4.6818 | 5.5 |
| 12 | 20.041 | 4.4270 | 5.0 |
| 13 | 20.380 | 4.3541 | 11.1 |
| 14 | 21.140 | 4.1993 | 3.5 |
| 15 | 21.939 | 4.0481 | 58.3 |
| 16 | 22.901 | 3.8802 | 13.8 |
| 17 | 23.340 | 3.8082 | 100.0 |
| 18 | 23.960 | 3.7110 | 3.3 |
| 19 | 24.480 | 3.6334 | 2.9 |
| 20 | 26.343 | 3.3805 | 3.6 |

Experimental

| | |
|---|---|
| Instrument: | Siemens D500 |
| Wavelength: | 0.1541 nm (CuK$_1$) |
| Range: | 30°–33° (2θ) |
| Power: | 40 mA/40 kV |
| Time: | 1°/min (0.02° step) |

For the treatment of Parkinson's disease, the stable polymorphic compound of the present invention may be administered to a patient in need of such treatment along with levodopa. A peripheral decarboxylate (DDC) inhibitor, such as carbidopa or benserazide may be optionally present.

The compound according to this invention may be given in different dosage forms for administering in any suitable enteral or parenteral way. The dosage forms, like tablets, pills, injection, liquids, and the like, may be manufactured by the known principles in the art. Once can use any pharmaceutically accepted additives, lubricants, fillers, and the like, to modify different properties of the dosage forms.

Catechol-O-methyltransferase (COMT) catalyzes the transfer of the methyl group from S-adenosyl-L-methionine to a number of compounds with catechol structures. This enzyme is important in the extraneuronal inactivation of catecholamines and drugs with catechol structures. COMT is one of the most important enzymes involved in the metabolism of catecholamines. It is present in most tissues, both in the peripheral and the central nervous system. The highest activities are found in the liver, intestine and kidney. COMT probably is present in soluble and membrane bound forms. The exact character of the two forms has not been established.

In Parkinson's disease the dopaminergic neurones, primarily the nigrostriatal neurones, are damaged, causing dopamine deficiency in the cerebral basal ganglia. This deficiency can be compensated by levodopa which is converted to dopamine in the central nervous system under the influence of DDC.

Today, levodopa treatment is almost invariably supplemented with a peripheral DDC inhibitor to inhibit early dopamine formation and thereby increase the cerebral levodopa concentration and decrease the peripheral side effects of dopamine.

In addition to DDC, COMT metabolizes levodopa, converting it 3-0-methyldopa (3-OMD). 3-OMD readily penetrates the blood-brain barrier via an active transport system. Alone it is therapeutically ineffective and detrimental when competing with levodopa. 3-OMD is accumulated in tissues because of its long half-life (about 15 hours) compared to levodopa (about 1 hour). The high activity of COMT clearly correlates with the poor efficacy of levodopa despite the presence of peripheral DDC inhibitor.

In addition to monoamine oxidase (MAO), COMT is a major enzyme participating in the amine metabolism. By inhibiting the metabolism of endogenous amines (dopamine, noradrenaline, adrenaline) in the brain the COMT inhibitors decrease decomposition of these compounds. Thus, they may be useful in the treatment of depression.

By inhibiting peripheral COMT effectively, COMT inhibitors direct the metabolic route of levodopa towards decarboxylation, forming thereby more dopamine which is important in the treatment of hypertension and heart failure.

The COMT inhibitor of the present invention, which inhibits formation of 3-OMD, may decrease the adverse effects of long-term use of levodopa. Furthermore, levodopa doses can be reduced. It has been shown that the dose of levodopa can be reduced by half or to one-third of the dose used without a COMT inhibitor. Since dosage of levodopa is individual, it is difficult to give any absolute dosage, but daily doses as low as 50 to 400 mg have been considered sufficient to start with.

The following example illustrates the invention.

EXAMPLE 1

The crude synthesis product (3.0 kg) prepared according to the method described in British patent application No. 8727854 was dissolved in 8.0 kg of acetic acid (98-100%) (or formic acid) containing 80 g of hydrogen bromide (or 40 g of hydrogen chloride) by heating to 90° C. The solution was slowly cooled to 20° C. and stirred for 20 h at 20° C. and finally for 6 h at 15° C. The crystalline product was filtered and washed carefully first with a cold (4° C.) mixture (1:1) of toluenea-cetic acid (1:1 v/v) and then with cold toluene (1:1). The product was dried in vacuum at 45° C. Yield of crystallographically pure A form of (E)-N,N-diethyl-2-cyano-3-(3,4-dihydroxy-5-nitro-phenyl) acrylamide was 2.4 kg (80%), m.p. 162-163° C.

We claim:

1. The crystallographically essentially pure polymorphic form A of (E)-N,N-diethyl-2-cyano-3-(3,4dihydroxy-5-nitrophenyl)acrylamide having the infrared spectrum in potassium bromide having the following absorption bands:

| Wave numbers (cm$^{-1}$) | Wave numbers (cm$^{-1}$) |
|---|---|
| 3339 | 1512 |
| 3092 | 1441 |
| 3066 | 1377 |
| 3039 | 1298 |
| 2981 | 1281 |
| 2938 | 1210 |
| 2217 | 1165 |
| 1628 | 1150 |
| 1607 | 800 |
| 1580 | 779 |
| 1544 | 740 |

2. A process for preparing crystallographically essentially pure polymorphic form A of (E)-N,N-diethyl-2-cyano-3-(3,4-dihydroxy-5-nitrophenyl) acrylamide having the infrared spectrum in potassium bromide having the following absorption bands:

| Wave numbers (cm$^{-1}$) | Wave numbers (cm$^{-1}$) |
| --- | --- |
| 3339 | 1512 |
| 3092 | 1441 |
| 3066 | 1377 |
| 3039 | 1298 |
| 2981 | 1281 |
| 2938 | 1210 |
| 2217 | 1165 |
| 1628 | 1150 |
| 1607 | 800 |
| 1580 | 779 |
| 1544 | 740 | which comprises crystallization of the crude N,N-diethyl-2-cyano-3-(3,4-dihydroxy -5-nitrophenyl acrylamide from lower aliphatic carboxylic acid containing a catalytic amount of hydrochloric or hydrobromic acid.

3. The process as claimed in claim 2, wherein said lower aliphatic carboxylic acid is acetic acid.

4. The process as claimed in claim 2, wherein said lower aliphatic carboxylic acid is formic acid.

5. A pharmaceutical composition for inhibiting catechol-O-methyl-transferase, said composition comprising a catechol-O-methyl-transferase inhibiting amount of the crystallographically essentially pure polymorphic form A of (E)-N,N-diethyl-2-cyano-3-(3,4-dihydroxy-5-nitrophenyl)acrylamide of claim 1 and a pharmaceutically acceptable carrier.

6. A method for inhibiting catechol-O-methyl -transferase in a patient, said method comprising administering a catechol-O-methyl-transferase inhibiting amount of the crystallographically essentially pure polymorphic form A of (E)-N,N-diethyl-2-cyano-3-(3,4-dihydroxy-5-nitrophenyl)acrylamide of claim 1, to a patient in need of such treatment.

7. A method for the treatment of Parkinson's Disease, said method comprising administering a catechol-O-methyl-transferase inhibiting amount of the crystallographically essentially pure polymorphic form A of (E)-N,N-diethyl-2-cyano-3-(3,4-dihydroxy-5-nitrophenyl)acrylamide of claim 1; and a sufficient amount of levodopa to treat Parkinson's disease, to a patient in need of such treatment.

8. The method as claimed in claim 7, further comprising administering a sufficient amount of a peripheral decarboxylase inhibitor to inhibit early dopamine formation.

9. The method as claimed in claim 8, wherein said peripheral decarboxylase inhibitor is carbidopa.

10. The method as claimed in claim 8, wherein said peripheral decarboxylase inhibitor is benserazide.

* * * * *